United States Patent [19]

Tozzolino et al.

[11] Patent Number: 4,827,044

[45] Date of Patent: May 2, 1989

[54] PROCESS OF PREPARATION OF KETONES

[75] Inventors: Pierre Tozzolino, Morlaas; Gérard Cahiez, Paris, both of France

[73] Assignee: Societe Nationale Elf Aquitaine, France

[21] Appl. No.: 165,616

[22] Filed: Mar. 8, 1988

[30] Foreign Application Priority Data

Mar. 11, 1987 [FR] France ............................ 87 03307
Mar. 11, 1987 [FR] France ............................ 87 03308

[51] Int. Cl.$^4$ ............................................ C07C 45/45
[52] U.S. Cl. ........................... 568/319; 568/323; 568/354; 568/355; 568/364; 568/397; 568/407; 560/51; 558/440
[58] Field of Search ............... 568/319, 354, 323, 397, 568/407, 355, 364; 560/51; 558/440

[56] References Cited

U.S. PATENT DOCUMENTS 3,895,070 7/1975 Mori et al. ........................ 568/397
4,450,296 5/1984 Yoshida ............................ 568/397

FOREIGN PATENT DOCUMENTS 2292690 6/1976 France ............................ 568/407
55-130934 10/1980 Japan ............................ 568/407
59-199650 11/1984 Japan ............................ 568/407

OTHER PUBLICATIONS

Friour et al., Synthesis, #1, pp. 37–40 (1984).
Eberle et al., Tetrahedron Letter, vol. 21, pp. 2303–2304 (1980).

*Primary Examiner*—James H. Reamer
*Attorney, Agent, or Firm*—Ostrolenk, Faber, Gerb & Soffen

[57] ABSTRACT

Process of preparation of ketones by the reaction of an organo-metallic compound with a compound carrying a carbonyl, within a solvent, in the presence of a manganous salt as catalyst. The manganous salt is in the form of a double salt of Mn and an alkali metal cation.

11 Claims, No Drawings

PROCESS OF PREPARATION OF KETONES

The present invention relates to an improvement in the preparation of ketones. It relates more particularly to the preparation of various ketones by the action of an organo-metallic compound on a compound carrying one or more carbonyl groups.

The usefulness of ketones in general is well known; among standard methods for their preparation, that based on the use of an organo-metallic reactant is of great interest because it allows the preparation of various types of ketones, useful particularly in the pharmaceutical field, as well as in those relating to scents and perfumes. The route via organo-metallic compounds has formed the subject of various works, including among others those of Eberle and Kahle ("Tetrahedron Letters" vol. 21, p. 2303–2304, 1980) which describe the preparation at low temperature of ketones carrying various functions, such as halogens and esters. A clear advance was made in this field by the use of organo-manganous compounds which allow operation under easier and more convenient conditions. Thus according to G Cahiez ("L'Actualité, Chimique"), September 1984, pages 27–28) all kinds of ketones have been synthesised in ether or tetrahydrofuran, by the reaction $RMnX + R'COZ \rightarrow RCOR'$, R et R' being alkyls, alkenyls, aryls or alkynyls, X being a halogen and Z a group capable of combining with —MnX. The reaction can be carried out at temperatures from 0° to +10° C. instead of −50° to −70° C. which organomagnesium compounds require.

However, in the industrial field where the most practical R'COZ reactants are acid chlorides, the use of organomanganous compounds presents certain difficulties. A first disadvantage lies in that the especially practical solvent, THF (tetrahydrofuran), undergoes opening of its ring under the action of the acid chloride, in the presence of an organomanganous compound. Another disadvantage is that, in a solvent such as ether, the reaction only takes place well if the organomanganous compound is an iodide, that is RMnI, which is not acceptable from the economic standpoint.

When the reaction is carried out in hydrocarbons, for example the reduction of vinyl or aryl halides by means of organo-metallic compounds, the difficulties mentioned above can be avoided by the use of an organomagnesium compound in the presence of a catalyst comprising a manganese halide, in particular $MnCl_2$, as indicated by Cahiez at page 26 of the article cited above. The reaction can take place in THF or in ether and, depending upon the case, gives yields of about 80 to 95%. However, the application of this catalytic procedure to the Grignard reaction for the preparation of ketones is deceptive, because of yields which are much too low for industrial use.

The present invention provides a new and improved solution which allows the production of all kinds of ketones by the action of an organo-metallic compound on an organic compound carrying one or more carbonyl groups, at temperatures around the ambient temperature, within standard solvents for such a reaction. It renders possible the attainment of yields which are very satisfactory industrialy.

This process may consist in dissolving in the appropriate solvent an organo-metallic compound RMX, where R is an organic group, M is a metal of groups I-III and VI-VII of the Periodic Classification of the Elements and X is a halogen, adding to the solution obtained a salt of Mn in a catalytic quantity and mixing this solution with a solution, preferably in the same solvent, of a compound carrying one or more carbonyl groups, of the type R'COZ, where R' is an organic group similar to R or different from R, Z being any group capable of combining with —MX. The process is characterised in that the Mn salt serving as the catalyst is used in the form of a double salt of Mn with an alkali metal or ammoniacal cation.

Thus the catalyst according to the invention comprises a double manganous salt of the type $MnX_2.nM'Y$, where X is an anion, for example halogen, $\frac{1}{2}SO_4$, $\frac{1}{3}PO_4$, $BF_4$, $\frac{1}{3}BO_3\frac{1}{2}SiF_6$, $CH_3COO$-(acetic), preferably halogen, M' is an alkali metal and/or ammonium cation, Y is an anion of the same type as X but not necessarily identical, n being generally 1 to 4.

Very practical use can be made of double salts of Mn with $NH_4$ or quaternary ammonium, Na, K or Li, X and Y being halogens, where naturally Cl is the most economic. In particular, the anhydrous double salt $MnCl_2.2LiCl$ is of great utility for carrying out the invention.

The quantity of the catalyst to be employed can vary widely, but generally corresponds to 0.5 to 6 atoms of Mn per 100 moles of the reactant R'COZ and preferably from 1 to 5 atoms Mn/100 moles of this reactant; the best proportions are between 2 and 4 atoms of Mn, namely the quantity of the double salt $MnX_2nMY$ is such that is has 2 to 4 atoms of Mn per mole of R'COZ.

According to a variant of the invention, the activity of the catalyst can be further reinforced by the addition of a cuprous salt. The proportion by weight of this is preferably of the same order as that of the complex Mn salt. Such an addition is particularly useful when the group R of the organometallic compound utilised is hindered; the presence of Cu then allows increase in the yield of the ketone despite hindrance of the R group.

Due to the process of the invention, good yields at temperatures ranging from about −10° C. to +30° C. are obtained, the operation being particularly practical between −5° C. and +10° C. for monoketones and between about +10° C. and 30° C. in the case of diketones. It is possible to carry out everything in an economical solvent such as THF, without any alteration of this solvent.

The reaction:

or

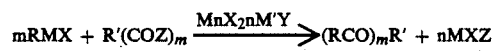

(m being 2 or 3), can be carried out with different organo-metallic compounds RMX, as indicated above, and more particularly with Grignard magnesium compounds, particularly RMgCl.

R can be any organic group compatible with the metal M and in particular a $C_1$ to $C_{20}$ alkyl, alkenyl or alkynyl, a $C_5$ or $C_6$ cycloalkyl or a $C_6$ to $C_{28}$ aryl or alkyl-aryl. These groups can carry substituents which are not reactive as regards the metal M.

R' is a group which like R can be an alkyl, alkenyl, alkynyl, cycloalkyl or aryl and it can carry substituents, particularly functions which do not react with RMX. By contrast, Z is an atom or group having affinity for the metal M, for example a halogen atom or a carbonyl. Thus, R'COZ can advantageously be a compound such as

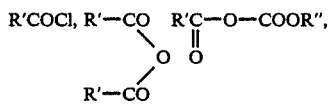

where R" is an alkyl, etc. For industrial practice, the most advantageous reactants are of the type R'COCl, that is the acid chlorides.

As regards possible substituents for R', they can be for example Cl, Br, —OR, —SR, —COOR, —CN, —CO etc. which permit the preparation of the corresponding functional ketones.

Thus the process of the invention allows easy preparation of a wide range of saturated, ethylenic, aromatic and acetylenic ketones, possibly carrying other functional groups, the production being carried out with very good yields. It will be understood that the duration of the reaction depends on the temperature, the nature of the organo-metallic compound and the acylating compound R'COZ, as well as that of the particular catalyst utilised; it can in particular vary from 0.5 to 10 hours, but it is generally possible to regulate the operative conditions so that the reaction is terminated in about 1 to 4 hours.

The excellent results given by the process of the present invention and which can be seen in the examples given below are especially unexpected because prior attempts to prepare ketones starting from organomanganous compounds, using the complex salt $MnCl_2.2LiCl$, proved to be very delicate and impossible to carry out industrially. These are described in Synthesis, No. 1, Jan. 1984, pages 37-38, by G Friour et al. It is true that, in contrast to the present invention, the complex salt in question was not used as a catalyst in the reaction of a magnesium atom with an acid chloride, but as a reactant in stoichiometric proportion for the preparation of an organomanganous compound starting from an organomagnesium co mpound. It is only the organomanganous compound once prepared which has been reacted with a compound R'COZ; it was necessary to operate in the presence of ether and at low temperature up to −80° C. (page 3 "Method C"); if THF is employed, its quantity should be minimal. At higher temperatures, the yields drop rapidly. In contrast, according to the present invention, several percent of $MnCl_2.2LiCl$ suffice as the catalyst, used in solution in THF with a compound R'COZ, for a progressive addition of a magnesium compound RMgX to this solution to produce a ketone RCOR' with good yields at a low temperature, for example 10° C., without any preliminary cooling.

The invention is illustrated by the nonlimitative examples which follow.

GENERAL MODE OF OPERATION IN THE EXAMPLES 3 mmoles of dry $MnCl_2$ and 6 mmoles of dry LiCl are added at ambient temperature to 50 ml of anhydrous THF. The mixture is then agitated to give complete dissolution of the salts and then 100 mmoles of RCOCl in 50 ml of THF are added. Then 100 mmoles of RMgX are introduced with the aid of a pump. The temperature of the reaction medium during the addition of the RMgX, namely the duration of this addition (generally 0 to +10° C. and 30 min) are indicated in Table III. It is important to maintain a vigorous agitation throughout all the duration of the introduction of the RMgX. After the latter, the agitation is maintained for 15 to 30 mins at ambient temperature and then the reaction medium is hydrolysed with dilute HCl solution. The product is then isolated according to customary techniques.

EXAMPLES 1 TO 5

The organo-metallic compound RMX here is the chloride or bromide of butyl magnesium, $C_4H_9MgCl$ (or Br); a test with butyl-lithium is carried out for comparison. The compound having the carbonyl group, R'COZ, is a derivative of octanoic acid (caprylic), $C_7H_{15}$-COOH, particularly the chloride (Z=Cl), anhydride or ester.

The catalyst is the double salt $MnCl_2.2LiCl$ employed at the ratio of 3 moles per 100 moles of BuMgCl or BuMgBr.

In the table of results below, the solvent of the solution of butyl-magnesium is indicated and that of the reaction medium to which the solution is added.

The yield of ketone $C_4H_9$—CO—$Cl_7H_{15}$, butyl heptyl ketone, are expressed with respect to the initial butyl-magnesium compound.

TABLE I

| Example n° | RMX solvent | $C_7H_{15}COZ$ | solvent | Yield % |
|---|---|---|---|---|
| 1 | BuMgCl/THF | $C_7H_{15}COCl$ | THF | 87 |
| 2 | BuMgBr/ether | " | " | 82 |
| 3 | BuLi/ether | " | Ether | 52 |
| 4 | BuMgCl/THF | $C_7H_{15}\underset{\underset{O}{\|\|}}{C}$—OCOEt | THF | 75 |
| 5 | BuMgCl/THF | $(C_7H_{15}CO)_2O$ | " | 22 |

Examples 1 and 2 show by comparison with the others that the best results are obtained with RMgCl (or Br) when the compound R'COZ is an acid chloride.

EXAMPLES 6 TO 20

The materials which are reacted are here butyl magnesium chloride and octanoic acid chloride, in tetrahydrofuran (THF) for the reaction:

As in the preceding examples, the quantities of the catalyst are expressed in molar percentages of the organo-metallic compound, that is in the number of Mn atoms per 100 moles of $C_4H_9MgCl$.

The yields of ketone are based on the quantities of magnesium compound used. The results are summarised in Table II.

TABLE II

| Example no | Nature of the catalyst | Quantity of the catalyst (mole %) | Temperature (°C.) | Duration of the addition of BuMgCl (in min) | Yield (%) |
|---|---|---|---|---|---|
| A/ Influence of the nature of the catalyst | | | | | |
| 6 | $MnCl_2$ | 3% | 0 to +10 | 30 | 60 |
| 7 | $MnCl_4Li_2$ | " | " | " | 87 |
| 8 | $MnBr_4Li_2$ | " | " | " | 84 |
| 9 | $Mn(OOC—CH_3)_2$ | " | " | " | 76 |

TABLE II-continued

| Example no | Nature of the catalyst | Quantity of the catalyst (mole %) | Temperature (°C.) | Duration of the addition of BuMgCl (in min) | Yield (%) |
|---|---|---|---|---|---|
| B/ Influence of the quantity of the catalyst ||||||
| 10 | MnCl$_4$Li$_2$ | 1% | 0 to +10 | 30 | 70 |
| 11 | " | 3% | " | " | 87 |
| 12 | " | 5% | " | " | 82 |
| C/ Influence of the speed of addition of BuMgCl ||||||
| 13 | MnCl$_4$Li$_2$ | 3% | 0 to +10 | 15 | 61 |
| 14 | " | " | " | 30 | 87 |
| 15 | " | " | " | 60 | 72 |
| D/ Influence of the temperature ||||||
| 16 | MnCl$_4$Li$_2$ | 5% | −5 | 30 | 85 |
| 17 | " | " | +10 | " | 82 |
| 18 | " | " | +20 | " | 82 |
| 19 | Without catalyst | | −5 | " | 36 |
| 20 | " | | +10 | " | 27 |

Examples 7, 11 and 14 carried out under the same conditions as example 6 show the considerable improvement in the yield due to the use of a complex of MnCl$_2$ with 2 moles of LiCl, in place of MnCl$_2$ alone. In effect, the yield in examples 7, 11 and 14 rises to 87% in contrast to 60% for example 6, or 1.45 times the latter.

Examples 19 and 20 where no catalyst was used lead to very low yields.

EXAMPLES 21 TO 35

Various ketones have been prepared according to the reaction

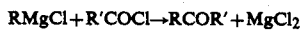
RMgCl + R'COCl → RCOR' + MgCl$_2$ with 3 moles of MnCl$_4$Li$_2$ per 100 moles of RMgCl utilising different R and R' groups. Table III summarises the results obtained.

of the use at R or R' of a hindered alkyl, tertiary butyl in this instance.

It is interesting to confirm that the presence of an atom or functional group Q in R', (examples 31 to 35), does not prevent the preparation of a ketone provided with this atom or group Q. If in this case R' is of the type Q-(CH$_2$)$_n$, the yield is even better if n is larger.

These results allow the person skilled in the art to employ the most favourable working conditions in each particular case.

EXAMPLES 36-37

Operating as in examples 23 and 27, the action of CuCl employed in conjunction with MnCl$_2$2LiCl has been tested, each in a ratio of 3 moles per 100 moles of RMgCl. The yields in ketone are then:

| Example | R | R' | Yield % |
|---|---|---|---|
| 23 | Hept | t-Bu | 52 |
| 36 (+CuCl) | " | " | 98 |
| 27 | t-Bu | Hept | 27 |
| 37 (+CuCl) | " | " | 80 |

It is possible to confirm, both for a hindered R (t-Bu) and for a hindered R' (t-Bu), the presence of CuCl considerably increases the yield of ketone.

In the examples which follow, the preparation of diketones by the same procedure of the invention has been illustrated. This is the operative mode employed.

4 g of dry MnCl$_2$ and 1.5 g of dry LiCl are added at ambient temperature to 500 ml of anhydrous THF. The mixture is then agitated until complete dissolution of the salts and then 1 mole of R'(COCl)$_2$ in 500 ml of THF is added. Then 2 moles of RMgX are progressively introduced by means of a pump. The temperature of the reaction medium during the addition of the RMgX is from 25° to 30° C. It is important to maintain a vigorous

TABLE III

| Example no | R | R' | Temperature (C.°) | Duration of the addition of RMgCl (min) | Yield of isolated ketones (%) |
|---|---|---|---|---|---|
| A/ Saturated and unsaturated ketones ||||||
| 21 | Bu | Hept | 0 to +10 | 30 | 87 |
| 22 | Hept | i-Pr | " | " | 94 |
| 23 | " | t-Bu | " | " | 52 |
| 24 | " | Me$_2$C=CH | " | " | 79 |
| 25 | Bu | Ph | 0 | 45 | 85 |
| 26 | i-Pr | Hept | " | 30 | 74 |
| 27 | t-Bu | " | 0 to +10 | " | 27 |
| 28 | Me$_2$C=CH[a] | " | 0 | 40 | 73 |
| 29 | Ph | Bu | +25 to +30 | 30 | 70 |
| 30 | i-Pent[b] | i-Bu | 0 to +10 | " | 83 |
| B/ Functional ketones ||||||
| 31 | Bu | —(CH$_2$)$_3$COOEt | 0 to +10 | 30 | 62 |
| 32 | " | —(CH$_2$)$_4$COOEt | " | " | 83 |
| 33 | " | —(CH$_2$)$_3$Cl | " | " | 58 |
| 34 | " | —(CH$_2$)$_{10}$Br | " | " | 71 |
| 35 | " | —(CH$_2$)$_6$CN | " | " | 84 |

[a] Me$_2$C=CHMgBr
[b] In this case the reaction has been carried out by adding i-PentMgBr in solution in ether (1.1 N).

In the course of this work, it was found that with R' comprising a phenyl (example 25) it is preferable to operate at 0° C. and for somewhat longer (45 min) than in the other cases. It is the same with an alkenyl at R (example 28). In contrast, operation can take place nearer 25° to 30° C. when R is a phenyl (example 29).

The steric hindrance plays a role which can be seen in examples 23 and 27, where the yield is reduced because agitation throughout the entire duration of the introduction of the RMgX. After the latter, the agitation is maintained for a further 1 hour at ambient temperature and then the reaction medium is hydrolised with a dilute HCl solution. The product is then isolated according to customary techniques.

EXAMPLE 38

According to the general mode of operation described above, 203 g (1 mole) of isophthaloyl dichloride in 500 ml of THF is reacted with 274 g (2 moles) of phenyl magnesium chloride. The subsequent hydrolysis is effected with the aid of a dilute hydrochloric acid solution. By cooling, the diketone crystalises. 1,3-dibenzoyl-benzene is obtained in a yield of 75%. The product is recrystallised from ethanol. White crystals are obtained, the melting point of which is 100° C., which corresponds to the formula:

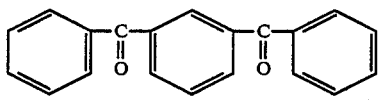

EXAMPLE 39

By replacing the phenyl magnesium chloride with 4-methyl-phenylmagnesiumchloride, 1,3-di(4-methyl-benzoyl)-benzene is obtained with a yield of 70%. The product is recrystallised from ethanol. White crystals which melt at 126° and 127° C. are obtained.

EXAMPLE 40

The replacement of the isophthaloyl dichloride with hexanoyl dichloride gives 1,6-diphenylhexanedione-1,6 in a yield of 65%. After recrystallisation, the product melts at 106° C.

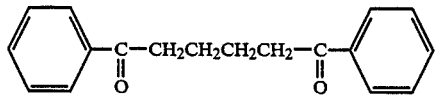

EXAMPLE 41

In example 38, the phenyl magnesium chloride is replaced by butyl magnesium chloride. 1,3-dipentanoyl-benzene is obtained in a yield of isolated product of 75%.

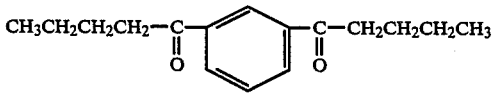

EXAMPLE 42

Use of the diketone in example 38. It is transformed into the diol and then into the diene. These two reactions can be carried out without isolating the intermediate diketone.

After reaction of the phenyl magnesium chloride, the reaction medium is cooled to $-10°$ C. and 27 g (1.20 moles) of methyllithium are added. The reaction is pursued for 2 hours, the temperature slowly rising to the ambient temperature. Then hydrolysis of the medium is carried out with dilute hydrochloric acid at a temperature in the range from $-10°$ to $0°$ C.

After washing, the THF is eliminated and the residue is taken up by 500 ml of toluene to which has been added 0.2 g of an acid type catalyst, such as paratoluenesulphonic acid, and the whole is taken to reflux for 1 hour 30 minutes. The medium is neutralised and the toluene eliminated under reduced pressure. The crude reaction product is a viscous oil of a yellow orange colour. It is taken up in boiling ethanol and, on cooling the solution, colourless crystals of 1,3-di[(phenyl)-ethenyl]-benzene are obtained, the melting point of which is 46° C.

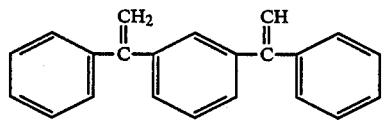

EXAMPLE 43

The diketone obtained in example 39 is treated according to the mode of operation of example 42. After recrystallisation from ethanol, white crystals of 1,3-di[(4-methyl-phenyl)ethenyl]-benzene are obtained, which melt at 66° C. The two dienes obtained in examples 42 and 43 are converted, after reaction with an alkyllithium such as sec.butyllithium, into organolithium derivatives which are commonly utilised as initiators in the polymerisation of dienes, such as butadiene or isoprene, in the 1-4 configuration favourable to the properties of the elastomer which results.

We claim:

1. A process for the preparation a ketone which comprises reacting a compound RMgX with a carboxylic acid derviative $R'(COZ)_m$ in solution and in the presence of a catalyst wherein R and R' are individually selected from the group consisting of 1 to 20 carbon atoms alkyl, alkenyl or alkynyl group, 5 to 6 carbon atom cycloalkyl group or a 6 to 28 carbon atom aryl or alkylaryl group, or R' is said alkyl group substituted by —COOR″, Cl, Br or CN where R″ is alkyl, X is Cl or Br, M is 1 to 3, Z is Cl, R'COO— or —O—CORR″, and in which said catalyst is $MnCl_2.2liCl$ or $MnBr_2.2LiBr$ and is present in the amount of 0.5 to 6 mols per 100 of said compound RMgX.

2. The process of claim 1 in which the reaction is carried out at a temperature in the range of $-10°$ to $+30°$ C.

3. The process according to claim 2 in which the amount of said catalyst is 2 to 4 mols per 100 mols.

4. The process of claim 1 in which the reaction medium contains a catalytic amount of a cuprous salt.

5. A process according to claim 4 in which the cuprous salt is CuCL and is present in an amount of 0.5 to 6 mols per 100 mols of said compound RMgX.

6. A process according to claim 1 wherein the solvent is tetrahydrofuran.

7. A process according to claim 1 in which R is alkyl of 3 to 7 carbon atoms.

8. A process according to claim 7 in which X is Cl.

9. A process according to claim 1 in which R is phenyl or methylphenyl.

10. Process according to claim 1 in which R is 1,1-dimethylvinyl.

11. Process according to claim 1 in which said carboxylic acid derivative is isophthaloyl dichloride or hexanoyl dichloride.

* * * * *